United States Patent
Yamashita et al.

(10) Patent No.: US 6,780,403 B1
(45) Date of Patent: Aug. 24, 2004

(54) DEODORANTS

(75) Inventors: Osamu Yamashita, Wakayama (JP); Shigeyoshi Tanaka, Wakayama (JP); Toru Tsutsumi, Tokyo (JP); Hirohiko Ishida, Tokyo (JP); Keiji Tsuchikura, Tokyo (JP); Toyoki Hagura, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/030,112

(22) PCT Filed: Jul. 12, 2000

(86) PCT No.: PCT/JP00/04670

§ 371 (c)(1),
(2), (4) Date: May 23, 2002

(87) PCT Pub. No.: WO01/07002

PCT Pub. Date: Feb. 1, 2000

(30) Foreign Application Priority Data

| Jul. 26, 1999 | (JP) | 11-211070 |
| Apr. 6, 2000 | (JP) | 2000-104720 |
| Jun. 29, 2000 | (JP) | 2000-196030 |

(51) Int. Cl.⁷ ............................ A61K 7/32; A61K 7/00
(52) U.S. Cl. ..................... 424/65; 424/400; 424/401
(58) Field of Search ..................... 424/65, 400, 401

(56) References Cited

U.S. PATENT DOCUMENTS

| 4,405,354 A | * | 9/1983 | Thomas, II et al. | 424/76.1 |
| 4,919,925 A | * | 4/1990 | Ueda et al. | 424/76.1 |
| 5,356,803 A | * | 10/1994 | Carpenter et al. | 435/200 |
| 5,718,887 A | | 2/1998 | Wolf et al. | |

FOREIGN PATENT DOCUMENTS

| JP | 36-9898 | 7/1961 |
| JP | 54-5041 | 1/1979 |
| JP | 56-142206 | 11/1981 |
| JP | 57-500590 | 4/1982 |
| JP | 61-193665 | 8/1986 |
| JP | 62-6449 | 2/1987 |
| JP | 4-257514 | 9/1992 |
| JP | 5-84283 | 4/1993 |
| JP | 5-255059 | 10/1993 |
| JP | 6-181972 | 7/1994 |
| JP | 8-26957 | 1/1996 |

OTHER PUBLICATIONS

JP–A 56–142206 English Abstract.
JP–A 54–5041 English Abstract.

* cited by examiner

*Primary Examiner*—Shelley A. Dodson
(74) *Attorney, Agent, or Firm*—Oblon, Spivak, McClelland, Maier & Neustadt, P.C.

(57) ABSTRACT

The present invention provides a liquid deodorant suitable for deodorization of spaces and fiber products, and a hair cosmetic and skin cosmetic having a high deodorization effect. Here any of the hair cosmetic and skin cosmetic may be that referred to as a body deodorant. Namely, the present invention provides a deodorant comprising a deodorant organic dibasic acid composed of an organic dibasic acid and/or salt thereof having a difference between the first acid dissociation index (hereinafter, abbreviated as first acid dissociation index and the second acid dissociation index (hereinafter, abbreviated as second acid dissociation index or $pK_2$) of 1.7 or more a 25° C.

18 Claims, No Drawings

DEODORANTS

FIELD OF THE INVENTION

The present invention relates to a deodorant, hair cosmetic and skin cosmetic. More particularly, both of the hair cosmetic and skin cosmetic may be called a body deodorant.

BACKGROUND ART

Deodorants moderate discomfort odor together with an aromatic and play an important role for comfortable life. Body odors such as a sweat odor, hircismus, foot odor, scalp odor and the like, and life odors in home including a tobacco odor and pet odor tend to be adsorbed by bodies including hair and fiber products as well as bodies and spaces, causing a desire for simple deodorization methods. As disclosed in JP-A Nos. 61-193665 and 4-257514, a deodorizing component such as vegetable extracts and the like is compounded in a deodorant and a composition is allowed to have a buffering ability with the aid of lactic acid, tartaric acid, citric acid or the like and a sodium salt thereof, however, sufficient effects are not obtained. Though a masking method with a perfume is general, it has problems such as an insufficient effect, increase in discomfort as a reverse effect, and the like.

JP-A No. 6-181972 describes a tobacco deodorant having a buffering ability composed of a citric acid-citrate, JP-B No. 62-6449 described a deodorant wet napkin composed of a surfactant and citric acid, acetic acid or succinic acid, and JP-A No. 5-255059 describes masking with a lignaloes wood spirit oil.

The masking described in JP-A No. 5-255059 shows insufficient effects such as too strong masking perfume and the like.

Substances having a buffering ability such as citric acid and the like described in JP-A No. 6-181972 and JP-B No. 62-6449 manifest a deodorization effect only on basic discomfort odors of tobacco, fish and the like. Discomfort odors are classified into acidic odors typically including lower aliphatic acids, basic odors typically including ammonia, and sulfur-based odors typically including mercaptan. Discomfort odors are often complex odors thereof, and the deodorants described in JP-A No. 6-181972 and JP-B No. 62-6449 cannot provide an excellent deodorization effect against all of the above-mentioned three discomfort odors.

SUMMARY OF THE INVENTION

An object of the invention is to provide a liquid deodorant suitable for deodorizing spaces and fiber products.

Another object of the invention is to provide a hair cosmetic and skin cosmetic having a high deodorization effect. Hereinafter, any of the hair cosmetic and skin cosmetic may be one called a body deodorant.

The present invention provides a deodorant comprising an organic dibasic acid and/or a salt thereof having a difference between the first acid dissociation index (hereinafter, abbreviated as first acid dissociation index or $pK_1$) and the second acid dissociation index (hereinafter, abbreviated as second acid dissociation index or $pK_2$) of 1.7 or more at 25° C., namely, comprising a deodorant organic dibasic acid composed of at least one of the above-mentioned organic dibasic acid and salt thereof.

Further, it has been found that the above-mentioned deodorant organic dibasic acid has an excellent deodorization ability, and resultantly, a deodorant composition for spaces and fiber products, a hair cosmetic and a skin cosmetic containing the above-mentioned component are provided.

The above-mentioned organic dibasic acid preferably has a second acid dissociation index of 6 to 8. Desirably, the above-mentioned deodorant has a water content of 80 to 99% by weight.

The present invention provides a deodorant composition comprising the above-mentioned deodorant and a surfactant in an amount of 0.01 to 10% by weight. The above-mentioned deodorant composition may further comprise a perfume in an amount of 0.001 to 2.0% by weight.

The present invention also provides a spray mode deodorant article composed of a spray mode vessel filled with the above-mentioned deodorant.

Further, the present invention provides a hair cosmetic containing the above-mentioned deodorant organic dibasic acid.

Furthermore, the present invention provides a body deodorant containing the above-mentioned deodorant organic dibasic acid.

The present invention provides a skin cosmetic comprising the above-mentioned deodorant organic dibasic acid.

The present invention provides a use of the above-mentioned deodorant organic dibasic acid as a deodorant. Preferably, the above-mentioned use is an application for clothing or body, or hair or skin.

The present invention provides a deodorization method of applying the above-mentioned deodorant organic dibasic acid to an object to be deodorized. Preferable is a method wherein the above-mentioned object is clothing or body, or hair or skin.

The present invention provides a body deodorant composition containing the above-mentioned deodorant and bactericide or sweat controlling agent.

The present invention provides a sheet containing the above-mentioned body deodorant.

The present invention provides a deodorization method of pasting the above-mentioned sheet in dry or wet condition to a body or wiping a body with the above-mentioned sheet.

EMBODIMENTS OF THE INVENTION

The organic dibasic acid used as a deodorant in the present invention is selected from organic dibasic acids and/or salts thereof having a difference between the first acid dissociation index and the second acid dissociation index of 1.7 or more at 25° C. (hereinafter, described as deodorant organic dibasic acid). The acid dissociation index can be measured, for example, by a method (A) described in The Journal of Physical Chemistry vol. 68, number 6, page 1560 (1964). More simply, a method (B) of measuring by using a potential difference automatic titration apparatus manufactured by Kyoto Electronics Manufacturing Co., Ltd. (for example, AT310J and the like) can be used.

Further, previously obtained data may also be used. For example, maleic acid (first acid dissociation index 1.75, second acid dissociation index 5.83) is selected based on the acid dissociation index described in Chemical Handbook (C) (revision 3-rd ed., Jun. 25, 1984, Maruzen Co., Ltd.) edited by The Chemical Society of Japan. Further, the organic dibasic acid can be selected based on data bases (D) such as pKa BASE of Compudrug, and the like. The first acid dissociation index and the second acid dissociation index of the organic dibasic acid may be determined by any of the methods (A) to (D). According to the method (D), more specific physical properties and the first acid dissociation index and the second acid dissociation index of the deodorant organic dibasic acid of the present invention are shown in Tables 1 and 2.

TABLE 1

| | (25° C.) | | |
|---|---|---|---|
| Deodorant organic dibasic acid | First acid dissociation index ($pK_1$) | Second acid dissociation index ($pK_2$) | Difference |
| Trans-1,2-cyclopentandicarboxylic acid | 4.14 | 5.99 | 1.85 |
| Trans-1,2-cyclohexanedicarboxylic acid | 4.30 | 6.06 | 1.76 |
| Trans-1,2-cycloheptanedicarboxylic acid | 4.30 | 6.18 | 1.88 |
| Trans-1,2-cyclooctanedicarboxylic acid | 4.37 | 6.24 | 1.87 |
| Cis-1,2-cyclopropanedicarboxylic acid | 3.56 | 6.65 | 3.09 |
| Cis-1,2-cyclobutanedicarboxylic acid | 4.16 | 6.23 | 2.07 |
| Cis-1,2-cyclopentanedicarboxylic acid | 4.42 | 6.57 | 2.15 |
| Cis-1,2-cyclohexanedicarboxylic acid | 4.25 | 6.74 | 2.49 |
| Cis-1,2-cycloheptanedicarboxylic acid | 3.87 | 7.60 | 3.73 |
| Cis-1,2-cyclooctanedicarboxylic acid | 3.99 | 7.34 | 3.35 |
| 3,3-dimethyl-cis-1,2-cyclopropanedicarboxylic acid | 2.61 | 8.17 | 5.56 |
| 2,3-dimethylsuccinic acid | 3.92 | 6.00 | 2.08 |
| 2,3-diethylsuccinic acid | 3.63 | 6.46 | 2.83 |
| 2,3-di-t-butylsuccinic acid | 2.20 | 10.26 | 8.06 |
| 2-ethyl-3-methylsuccinic acid | 3.20 | 6.10 | 2.90 |
| Tetramethylsuccinic acid | 3.56 | 7.41 | 3.85 |
| Phenylsuccinic acid | 3.78 | 5.55 | 1.77 |
| 3,3-dimethylglutaric acid | 3.85 | 6.45 | 2.60 |
| 3,3-diethylglutaric acid | 3.67 | 7.42 | 3.75 |
| 3,3-dipropylglutaric acid | 3.65 | 7.48 | 3.83 |
| 3,3-diisopropylglutaric acid | 3.65 | 7.68 | 4.05 |
| 3-methyl-3-ethylglutaric acid | 3.62 | 6.70 | 3.08 |
| 3-isopropyl-3-methylglutaric acid | 3.78 | 6.92 | 3.14 |
| 3-t-buthyl-3-methylglutaric acid | 3.61 | 7.49 | 3.88 |
| 2-ethyl-2-(1-ethylpropyl)glutaric acid | 2.15 | 7.31 | 5.16 |
| 3-methyl-3-phenylglutaric acid | 4.12 | 6.17 | 2.05 |
| 3-ethyl-3-phenylglutaric acid | 3.89 | 6.95 | 3.06 |
| 3,3-diphenylglutaric acid | 4.02 | 6.81 | 2.79 |
| 3-phenyl-3-propylglutaric acid | 3.88 | 6.94 | 3.06 |

TABLE 2

| | (25° C.) | | |
|---|---|---|---|
| Deodorant organic dibasic acid | First acid dissociation index ($pK_1$) | Second acid dissociation index ($pK_2$) | Difference |
| 2-methylcyclohexyl-1,1-diacetic acid | 3.53 | 6.89 | 3.36 |
| 3-methylcyclohexyl-1,1-diacetic acid | 3.49 | 6.08 | 2.59 |
| 4-methylcyclohexyl-1,1-diacetic acid | 3.49 | 6.10 | 2.61 |
| cyclopentyl-1,1-diacetic acid | 3.80 | 6.77 | 2.97 |
| 3-methylcyclopentyl-1,1-diacetic acid | 3.79 | 6.74 | 2.95 |
| Cyclohexyl-1,1-diacetic acid | 3.49 | 7.08 | 3.59 |
| 2-methylmalonic acid | 3.05 | 5.76 | 2.71 |
| 2-ethylmalonic acid | 2.96 | 5.81 | 2.85 |

TABLE 2-continued

| | (25° C.) | | |
|---|---|---|---|
| Deodorant organic dibasic acid | First acid dissociation index ($pK_1$) | Second acid dissociation index ($pK_2$) | Difference |
| 2-isopropylmalonic acid | 2.92 | 5.88 | 2.96 |
| 2-t-butylmalonic acid | 2.92 | 7.04 | 4.12 |
| 2,2-dimethylmalonic acid | 3.03 | 5.73 | 2.70 |
| 2,2-diethylmalonic acid | 2.15 | 7.42 | 5.27 |
| 2,2-dipropylmalonic acid | 1.86 | 7.18 | 5.32 |
| 2,2-diisopropylmalonic acid | 2.12 | 8.85 | 6.73 |
| 2-ethyl-2-methylmalonic acid | 2.20 | 6.55 | 4.35 |
| 2-ethyl-2-isopropylmalonic acid | 2.03 | 8.10 | 6.07 |
| Maleic acid | 1.75 | 5.83 | 4.08 |

As a compound having a surface active ability, alkyl or alkenylsuccinic acids carrying an alkyl chain or alkenyl chain having 8 to 18 carbon atoms, and the like are listed. These have a first acid dissociation index of around 4.1 and a second acid dissociation index of around 6.1.

As substances which can be synthesized easily with a deodorant organic dibasic acid, Diels-Alder reaction products of a diene compound such as isoprene, cyclopentadiene, myrcene and the like with a dienophile compound such as maleic acid, citraconic acid and the like are listed. 5-norbornene-2,3-dicarboxylic acid is exemplified. As these compounds, those obtained by hydrogenating a double bond newly produced by the reaction can also be used. As other compounds which can be synthesized, those obtained by acetalization, ketalization and carbonation of tartaric acid with an aldehyde, ketone and phosgene are listed.

Of them, more preferable are those having a second acid dissociation index of 6 to 8, and specifically, cis-1,2-cyclooctanedicarboxylic acid, cis-1,2-cycloheptanedicarboxylic acid, cis-1,2-cyclohexanedicarboxylic acid, cis-1,2-cyclopentanedicarboxylic acid, cis-1,2-cyclobutanedicarboxylic acid, cis-1,2-cyclopropanedicarboxylic acid, trans-1,2-cyclooctanedicarboxylic acid, trans-1,2-cycloheptanedicarboxylic acid, trans-1,2-cyclohexanedicarboxylic acid, trans-1,2-cyclopentanedicarboxylic acid, alkyl or alkenylsuccinic acids carrying an alkyl chain or alkenyl chain having 8 to 18 carbon atoms, and the like are selected. Those having a condensed ring structure are particularly preferable.

The above-mentioned deodorant organic dibasic acid may also be a salt, and the counter salt is selected from alkali metal salts, alkaline earth metal salts, zinc salts, aluminum salts, ammonium salts and the like, and preferably, salts of alkali metals such as potassium and sodium are selected. These salts maybe a mono-salt, di-salt or a mixture thereof. Further, they may also be contained in the form of an acid together with the corresponding base.

(Deodorant for Space and Fiber Product)

In the deodorant of the present invention, the content of a deodorant organic dibasic acid which is an effective ingredient is 0.005% by weight or more, preferably from 0.01 to 20% by weight based on the deodorant, and particularly when used as a spray mode deodorant, the compounding amount is preferably from 0.01 to 10% by weight, most preferably from 0.01 to 5.0% by weight. A deodorant organic dibasic acid can be used alone or in admixture.

The deodorant of the present invention contains a deodorant organic dibasic acid, and can also be used in combination of other deodorant. Further, a usual additive such as an antioxidant, a pH controlling agent, a preservative, a perfume, a surfactant, a coloring matter, a ultraviolet absorber and the like can also be added.

The deodorant can be in the form of liquid, powder, gel, particle and the like depending on use, and the liquid form is most preferable. The deodorant of the present invention is effective for tobacco odor, sweat odor, pet odor, cooking odor and the like, therefore, most preferable is a method of deodorization in which the deodorant is charged in a spray mode vessel and sprayed onto a deodorization object such as space and fiber product, in particular.

When a sufficient deodorization effect is going to be obtained, and when used as a spray mode deodorant for fiber products, the water content of the deodorant is from 80 to 99% by weight, preferably from 85 to 96% by weight not to damage the fiber. In the present invention, ethanol is preferably compounded for sterilization and antimicrobial activity and, in the case of fiber deodorization, for easy evaporation of a liquid deodorant from a fiber product after treatment for drying, and the compounding amount thereof is from 1 to 15% by weight, more preferably from 2 to 12% by weight. As this ethanol, denatured ethanol can be used, and particularly, 8-acetylated saccharose-denatured ethanol or polyoxyethylene alkyl ether sodium sulfate-denatured ethanol is preferably used. Most preferably, the total amount of water and ethanol occupies 90% by weight to 99.5% by weight of a deodorant.

The deodorant of the present invention preferably contains a surfactant such as an anionic surfactant, nonionic surfactant, cationic surfactant or ampholytic surfactant carrying one or two alkyl or alkenyl groups having 8 to 22 carbon atoms, and an anionic surfactant or a nonionic surfactant is more preferable. The anionic surfactant is an anionic surfactant carrying an alkyl or alkenyl group having 8 to 18 carbon atoms, and specific examples thereof are salts of alkylbenzenesulfonic acid, salts of alkylsulfates, salts of polyoxyethylene alkyl ether sulfates having an ethylene oxide average addition mol number (hereinafter, referred to as EOp) of 1.0 to 20.0, salts of polyoxyethylene alkyl ether acetic acid having an EOp of 1.0 to 20.0, salts of dialkyl-sulfosuccinic acid or salts of polyoxyethylenealkylsulfosuc-cinic acid having an EOp of 0 to 8.0, and the nonionic surfactant is a nonionic surfactant carrying an alkyl or alkenyl group having 8 to 18 carbon atoms, and specific examples thereof are alkylglucosides having an average degree of sugar condensation of 1.0 to 2.0, polyoxyethylene alkyl ethers having an EOP of 1.0 to 40.0, polyoxyethyl-eneglycerides having an EOP of 1.0 to 40.0, polyoxyethyl-enesorbitan fatty esters, polyoxyethylenesorbitol fatty esters and amine oxides of mono-long chain alkyl type. Of these surfactants, when used as a deodorant of spray mode for space, it is preferable to use an alkyl glycodise having a degree of polymerization of a glucose residue of 1.2 to 1.8 in which one alkyl group or alkenyl group having 8 to 18 carbon atoms is added to 1-position of glucose, since then an effect by a perfume described later is improved. When used as a deodorant for fiber products, it is preferable to use a monoalkyldimethylamine oxide carrying an alkyl group having 8 to 18 carbon atoms and a fatty amide propyldim-ethylamine oxide. The compounding amount of these surfactants in a deodorant is preferably from 0.005 to 10% by weight, particularly preferably less than 5% by weight, and further, it is more preferable to compound an anionic surfactant and a nonionic surfactant in a total amount of 0.05 to 3% by weight.

The present invention can obtain a more suitable deodorization effect by compounding a perfume in an amount of 0.001 to 2% by weight, more preferably of 0.005 to 1% by weight, most preferably of 0.01 to 1% by weight. Though a perfume may be used as a single perfume body, it is preferable to use a mixed perfume. Regarding specific perfume components constituting a perfume, listed as perfume components having a mint-based perfume are 1-carbon, 1-menthone, 1-menthol and the like, and additionally, mint oil, peppermint oil, spearmint oil and the like are listed as natural essential oils, and listed as perfume components having a citrus-based perfume are limonene, citral, dihydromicenol and the like, and additionally, lemon oil, orange oil, lime oil, grape fruit oil, bergamot oil, lemon grass oil and the like are listed as natural essential oils. Further, listed as perfume components having a herb-based perfume are methyl salicylate, thimol, 1,8-cineole, linalool, citronellol, geraniol, terpineol, camphor and the like, and additionally, eucalyptus oil, geranium oil, citronella oil and the like are listed as natural essential oils, and listed as perfume components having a woody-based perfume are $\alpha,\beta$-pinene and the like, and additionally, cypress oil, cedar oil, pine oil, hiba oil and the like are listed as natural essential oils.

Of these perfume components, 1-carbon, geraniol, citral, thimol, 1,8-cineole, peppermint oil, spearmint oil, lemon grass oil and hiba oil have an antimicrobial activity, therefore, they are particularly preferable perfumes when used, for example, for deodorizing fiber products since these perfumes suppress generation of a discomfort order due to proliferation of microorganisms and the like from sebum and sweat components. In the present invention, it is preferable that the above-mentioned perfume components having an antimicrobial activity occupy 3 to 100% by weight, particularly 10 to 100% by weight of all perfume components. It is preferable to compound perfumes diluted in one or more compounds selected from 2-methyl-2,4-dihydroxybutane, 2-methyl-2,4-dihydroxypentane, 2,4-dihydroxybutane, dipropylene glycol and tripropylene glycol. In the liquid deodorant of the present invention, lower (having 3 to 4 carbon atoms) alcohols such as isopropanol and the like, polyhydric alcohols (having 2 to 12 carbon atoms) such as ethylene glycol, propylene glycol, glycerine, sorbitol and the like, and salts of aromatic sulfonic acids such as p-toluenesulfonic acid salt, m-xylenesulfonic acid salt and the like, can be compounded further as a solubilizer. Further, edible coloring matters, thickening agents and the like may be compounded if necessary, and it is preferable to compound antiseptic and antifungal agents such as methylparavene, sodium benzoate, proxel BDN and the like. It is preferable that the deodorant of the present invention has a pH of 5.0 to 9.0, particularly of 6.0 to 8.0. The liquid deodorant of the present invention is preferably filled in a spray vessel, and for example, it is preferable to use an accumulating type trigger excellent in liquid drip preventing property and spray uniformity as shown in FIG. 1 in JP-U No. 4-37554 from a vessel equipped with a mist type spray manifesting a spray amount of 0.2 ml to 0.5 ml per one stroke as shown in FIGS. 1, 3 and 4 in JP-A No. 50-78909.

(Hair Cosmetic)

The content of a deodorant organic dibasic acid in a hair cosmetic of the present invention is from 0.001 to 50% by weight (hereinafter, simply described as %), preferably from 0.001 to 30%, further from 0.01 to 10%. When a deodorant organic dibasic acid of the present invention is contained in the form of a salt, the content is defined in terms of an organic dibasic acid corresponding its salt.

The hair cosmetic of the present invention preferably contains a perfume in addition to a deodorant organic dibasic acid as an effective ingredient since then a deodorization effect is further reinforced. The content of a perfume in a hair cosmetic is from 0.001 to 2%, preferably from 0.005 to 1%, particularly from 0.01 to 1%. Though a perfume may be used as a single perfume body, it is preferable to use a mixed perfume. Specific examples of perfume components constituting a mixed perfume include natural essential oils such as α-pinene, β-pinene, methylanthrenylate, isobutylquinoline, eugenol, aldehyde C-10, coumarin, vanillin, trypral, cis-3-hexenol, α-ionone, β-ionone, γ-ionone, α-isomethylionone, allylionone, α-methylionone, β-methylionone, γ-methylionone, α-irone, β-irone, γ-irone, methylionone-G, Sandalmysolecore, γ-undecalactone, α-Damaskon, β-Damaskon, γ-Damaskon, α-Dynaskon, β-Dynaskon, Lilial, Chuberose, Caranal, Anbroxane, p-cresol, Malakja, Mosscins, Olivanamresinoid, geranylnitrile, phenoxyethyl alcohol, Florosa, heliotropin, anysil acetate, anysilacetone, acetyl eugenol, acetyl isoeugenol, pentalide, and cyclohexyl salicylate, mint oil, peppermint oil, spearmint oil, lemon oil, orange oil, lime oil, grape fruit oil, bergamot oil, lemon grass oil, eucalyptus oil, geranium oil, citronella oil, cypress oil, cedar oil, pine oil, hiba oil, lavender oil, Pachori oil and the like, 1-carbon, 1-menthone, 1-menthol, limonene, citral, dihydromilcenol, methyl salicylate, thimol, 1,8-cineol, linalool, citronellol, geraniol, terpineol, camphor and the like.

Particularly of these perfumes, α-pinene, β-pinene, methylanthrenylate, isobutylquinoline, eugenol, aldehyde C-10, coumarin, vanillin, trypral, cis-3-hexenol, α-ionone, β-ionone, γ-ionone, α-isomethylionone, allylionone, α-methylionone, β-methylionone, γ-methylionone, α-irone, β-irone, γ-irone, methylionone-G, Sandalmysolecore, aldehyde C-14 peach, α-Damaskon, β-Damaskon, γ-Damaskon, α-Dynaskon, β-Dynaskon, Lilial, Chuberose, Caranal, Anbroxane, p-cresol, Malakja, Mosscins, Olivanamresinoid, geranylnitrile, phenoxyethyl alcohol, Florosa, heliotropin, anysil acetate, anysilacetone, acetyl eugenol, acetyl isoeugenol, pentalide, and cyclohexyl salicylate are preferable since they show an excellent effect in masking of scalp odors and can add a function of masking a tobacco odor and cooking odor adhere to hair and head part and scalp odors other than discomfort odors such as a sweat odor and the like. It is preferable that they are compounded in a mixed perfume in a compounding ratio of 0.001 to 100%, particularly of 1 to 100%.

Of these perfume substances, 1-carbon, geraniol, citral, thimol, 1,8-cineole, peppermint oil, spearmint oil, lemon grass oil and hiba oil have an antimicrobial activity, therefore, they are particularly preferable perfumes since they suppress generation of a discomfort order due to proliferation of microorganisms and the like from sebum and sweat components adhered to hair and the like. In the present invention, these perfume substances can be compounded in a mixed perfume depending on the extend of an effect. It is preferable that the above-mentioned perfumes having an antimicrobial activity occupy 0.001 to 100%, particularly 1 to 100% of the whole perfume.

If necessary, other perfumes can be added to a perfume component, and the perfume component can be further diluted for use. In this case, as the diluting agent used, one or more compounds selected 2-methyl-2,4-dihydroxybutane, 2-methyl-2,4-dihydroxypentane, 2,4-dihydroxybutane, propylene glycol, dipropylene glycol, tripropylene glycol, ethanol, liquid paraffin, 3-methoxy-3-methylbutanol, diethyl phthalate and IP solvent are preferable.

Further, the antimicrobial agents other than single perfume bodies having an antimicrobial activity are not particularly restricted, and for example, zinc pyrthion (2-pyridinethiol-1-oxide zinc salt), aluminum chloride, zinc oxide, isopropylmethylphenol, benzalkonium chloride, trichlosane, chlorhexidine hydrochloride, halocarvane, benzotonium chloride, chlorhydroxyaluminum, allantoincloxyaluminum, zinc p-phenolsulfonate and the like may be contained in an amount of 0.001 to 50%, preferably of 0.01 to 30% in a hair cosmetic of the present invention.

The hair cosmetic of the present invention can further contain surfactants. These surfactants are preferably compounded for improving a hair regulating effect of the hair cosmetic and manifesting a sufficient washing effect, and additionally, for obtaining an effect of keeping a tobacco odor, cooking odor, sweat odor and the like. As specific examples of the surfactant, the following compounds are listed. First, examples of anionic surfactants include (1) glycolic acid N-alkyl (or alkenyl) amide sulfate ester salts, (2) alkylbenzenesulfonate salts, (3) alkyl (or alkenyl) ether sulfate salts, (4) alkyl (or alkenyl) sulfate salts, (5) olefinsulfonate salts, (6) alkanesulfonate salts, (7) saturated or unsaturated fatty acid salts, (8) alkyl (or alkenyl) ether carboxylic acids, (9) α-sulfonate salts or esters, (10) N-acylamino acid type surfactants, (11) phosphate mono or diester type surfactants, (12) sulfosuccinate esters, and the like.

Examples of nonionic surfactants include (13) polyoxyethylene alkyl (or alkenyl) ethers, (14) polyoxyalkylphenyl ethers, (15) polyoxypropylene alkyl (or alkenyl) ethers, (16) polyoxyalkylenealkyl (or alkenyl) ethers, (18) higher fatty acid alkanolamides or alkylene oxide adducts thereof, (19) saccharose fatty esters, (20) glycerine fatty monoesters, and the like. Of them, polyoxyethylene (1 to 30) lauryl ethers, glycerine fatty monoesters are preferable since they do not show a thickening action.

As the cationic surfactant, quaternary ammonium salts, particularly, mono-long chain or di-long chain type quaternary ammonium salts are preferable. Disclosed as the mono-long chain or di-long chain are alkyl salts, alkenyl salts, hydroxyalkyl salts, alkylcarbonylaminoalkyl groups, alkenylcarbonylaminoalkyl groups, alkylaminocarbonylalkyl groups, alkenylaminocarbonylalkyl groups, alkoxyalkxyl groups, alkenyloxyalkyl groups, aliphatic acyloxyalkyl groups, alkoxycarbonylalkyl groups, alkenyloxycarbonylalkyl groups and the like. Here, the alkyl portion or alkenyl portion may be linear or branched. More specifically, quaternary ammonium salts used in hair cosmetics and softeners described in JP-A Nos. 62-141176, 63-50574, 63-260991, 63-260992, 63-295765, 7-90773, 7-309723, 7-309724 and the like are listed. Preferable examples thereof include mono-long chain (linear or branched) alkyltrimethylammonium salts, di-long chain (linear or branched) alkyldimethylammonium salts, mono-long chain (linear or branched) alkyldimethylbenzylammonium salts, di-long chain (linear or branched) alkylmethylbenzylammonium salts, di-long chain (linear or branched) alkylmethylhydroxyethylammonium salts and the like.

Further, examples of ampholytic surfactants include imidazoline types, amideamino acid salts, carbobetaine types, alkylbetaine types, alkylamidebetain types, alkylsulfobetaine types and the like.

One or more surfactants may be used, and the compounding amount thereof is preferably from 0.05 to 30% by weight, particularly from 0.1 to 10% by weight based on the whole composition from the standpoints of foaming and the like.

In the hair cosmetic of the present invention, a silicone derivative can be compounded, to improve sensitivity and perfume remaining property. As this silicone derivative, dimethylpolysiloxane, methylphenylsiloxane, methylphenylpolysiloxane, amino-modified silicone, polyether-modified silicone, fatty acid-modified silicone, alcohol-modified silicone, aliphatic-modified silicone, epoxy-modified silicone and the like are listed.

One or more silicone derivatives may be used, and the compounding amount thereof is preferably from 0.01 to 15% by weight, particularly from 0.1 to 10% by weight based on the whole composition.

In the hair cosmetic of the present invention, a cationic polymer can be compounded to improve a sliding property and perfuming. Examples of this cationic polymer include cationized cellulose derivatives, cationic starch, cationized guar gum derivatives, diallyl quaternary ammonium salt polymers, diallyl quaternary ammonium salt/acrylamide copolymers, quaternarized polyvinylpyrrolidone derivatives, and the like. The hair cosmetic of the present invention is used in the form of liquid, powder, gel, particle and the like appropriately selected, and for a deodorization effect to be manifested effectively, a liquid form using water or lower alcohol as a solvent, preferably an aqueous lower alcohol solvent, further preferably an aqueous ethanol solution is advantageous. The pH value of the hair cosmetic of the present invention is not particularly restricted, and preferably from 4.5 to 9.0, particularly from 5.0 to 8.0 from the standpoint of sufficient manifestation of a deodorization effect.

In the hair cosmetic of the present invention, components usually used in a hair cosmetic can be appropriately used in addition to deodorant organic dibasic acids used as the effective ingredient and the above-mentioned components used if necessary. For example, oily substances such as fats and oils, esters and the like, humectants, thickening agents, solubilizers, pH controlling agents, organic solvents other than lower alcohol, film forming agents, polymer fine particles, antioxidants, chelating agents, coloring matters and the like can be used.

The deodorization effect of the hair cosmetic of the present invention is effective generally on hair washing agents, treatments used in a bath room, hair cosmetics for hair regulation, hair grow and the like, and particularly, when a deodorant organic dibasic acid and/or a salt thereof is used in hair regulating agents and hair growth and hair nourishing agents such as hair tonic, hair liquid, hair foam, styling agent, hair treatment, hair spray and the like which is not washed off, an excellent deodorization effect is obtained.

The hair cosmetic of the present invention is preferably filled in a spray vessel, and for example, it is preferable to use an accumulating type trigger excellent in liquid drip preventing property and spray uniformity as shown in FIG. 1 in JP-U No. 4-37554 from a vessel equipped with a mist type spray manifesting a spray amount of about 0.2 ml per one stroke as shown in FIGS. 1, 3 and 4 in JP-A No. 50-7809.

(Hair Cosmetic)

The content of a deodorant organic dibasic acid in a skin cosmetic of the present invention is from 0.001 to 50% by weight (hereinafter, simply described as %), preferably from 0.001 to 30%, further from 0.01 to 10%. When a deodorant organic dibasic acid of the present invention is contained in the form of a salt, the content is defined in terms of an organic dibasic acid corresponding its salt.

The skin cosmetic of the present invention can contain a bactericide or sweat controlling agent. As the bactericide, nonionic bactericides such as 3,4,4-trichlorocarbanilide (TCC), resorcin, phenol, hexachlorophene, triclosane, isopropylmethylphenol and the like, cationic bactericides such as benzalkonium chloride, benzetonium chloride, alkyltrimethylammonium chloride, zinc pyrithion and the like, and anionic bactericides such as sorbic acid, salicylic acid and the like, are listed. As the sweat controlling agent, aluminumhydroxy chloride, aluminum chloride, aluminum sulfate, basic aluminum bromine, aluminumphenolsulfonic acid, tannic acid, aluminumnaphthelenesulfonic acid, basic aluminum iodide, zirconium salts, aluminum-zirconium complex salts, zinc p-phenolsulfonate, and the like are listed. The bactericide is contained in an amount preferably of 0.01 to 5.0%, particularly of 0.05 to 3.0% based on the whole composition, and the sweat controlling agent is contained in an amount preferably of 0.1 to 30%, particularly of 1.0 to 15.0% based on the whole composition.

The pH value of the skin cosmetic of the present invention is not particularly restricted, and preferably from 4.5 to 9.0, particularly from 5.0 to 8.0 from the standpoint of sufficient manifestation of a deodorization effect. In the skin cosmetic of the present invention, components usually used in a skin cosmetic can be appropriately used in addition to deodorant organic dibasic acids used as the effective ingredient and the above-mentioned components used if necessary, For example, any compounding with components such as surfactants, oily substances such as fats and oils, esters and the like, humectants, thickening agents, solubilizers, oil gelling agents, metal oxides, organic ultraviolet absorbers, inorganic metal salts, organic metal salts, solubilizers, pH controlling agents, preservatives, organic solvents, polymer fine particles, antioxidants, chelating agents, coloring matters, drug components, perfumes and the like can provide various forms, for example, oil/water, water/oil type emulsified cosmetic, cream, cosmetic emulsion, cosmetic water, oily cosmetic, foundation, foot spray, sweat controlling spray, skin washing agent, liquid forms such as lotion, gel and the like, aerosol, pump spray, stick, rollon and the like.

The deodorization effect of the skin cosmetic of the present invention is effective generally on skin cosmetics such as body washing agents, cosmetics, foot spray, sweat controlling spray and the like, and particularly, when a deodorant organic dibasic acid is used liquid such as lotion, gel and the like, aerosol, pump spray, stick, rollon and the like which is not washed off, an excellent deodorization effect is obtained.

The deodorant of the present invention can effectively remove odors of amines, mercaptans, lower fatty acids and the like, and particularly, can provide space and fiber product deodorants excellent in a deodorization ability, hair cosmetics, and skin cosmetics.

(Body Deodorant)

The content of a deodorant organic dibasic acid in the body deodorant composition of the present invention is the same as in the above-mentioned hair cosmetic.

The body deodorant composition of the present invention is allowed to further contain a volatile solvent to increase use feeling.

As the volatile solvent, water, lower alcohols having 1 to 4 carbon atoms, cyclic dialkyl silicones having a polymerization number of 4 to 5 (particularly, cyclic dimethyl silicone (for example, "Silicone SH-344", manufactured by Dow Corning Tray Silicone Co., Ltd.)), linear dialkyl silicones having a polymerization number of 2 to 5 (particularly, linear dimethyl silicone (for example, "Silicone KF-96L (1cs)", manufactured by Shine-Etsu Chemical Co., Ltd.)), light paraffins (for example, "Nisseki Isosol 300", manufactured by Nippon Sekiyu Co., Ltd.) and the like are listed, and water and water-soluble solvents are preferable, particularly, water and lower alcohol are contained in a mixing ratio by weight of water/lower alcohol of 9/99 to 50/50, preferably of 10/90 to 50/50, particularly preferably of 20/80 to 45/55.

By controlling the water/lower alcohol ratio in the above-mentioned range, a dry and slippery feeling can be easily obtained by combination, for example, with a powder, in addition to an increased quick drying property. As the lower alcohol, ethanol and isopropanol are preferable, and particularly, ethanol is preferable. It is preferable that a volatile solvent is contained in a deodorant in an amount usually of 40 to 99%, preferably of 60 to 99%, particularly of 80 to 99%.

When a bactericide or sweat controlling agent is compounded in the body deodorant composition of the present invention, a further excellent deodorization effect is obtained, and though these may be used in combination in some cases, a bactericide is preferable. Here, as the bactericide, bactericides described in the above-mentioned skin cosmetic can be used. Of these bactericides, nonionic or anionic bactericides are preferable. As the sweat controlling agent here, sweat controlling agents described in the above-mentioned skin cosmetic can be used. Further, as the content of a bactericide or sweat controlling agent, contents described in the above-mentioned skin cosmetic can be used.

In the body deodorant composition of the present invention, a water-insoluble powder may be used in combination to obtain a more excellent dry or slippery feeling in touch of the skin.

Examples of the powder include organic powders such as polymer fine particles obtained by conducting dispersion polymerization of a vinyl monomer in a solvent using as a dispersing agent a polysiloxane compound having a radical-polymerizable group at one end (hereinafter, referred to as polymer bead S), silicone resins (KMP-590 (manufactured by Shin-Etsu Chemical Co., Ltd.), Tospearl 145 and Tospearl 2000 B (manufactured by GE Toshiba Silicones), Trayfil (manufactured by Tray Industries Inc.) and the like), nylon resins (SP-500 (manufactured by Tray Industries Inc.), polystyrene-based resins (Fine Pearl (manufactured by Sumitomo Chemical Co., Ltd.), TecPolymer SB (manufactured by Sekisui Plastics Co., Ltd.), Fine Powder SGP (manufactured by Soken Chemical & Engineering Co., Ltd), and the like), polyethylene resins (Flow Bead (manufactured by Sumitomo Seika Chemicals Co.,Ltd.) and the like), polymethyl methacrylate-based resins (Matsumoto Micro Sphere M (manufactured by Matsumono Yushi-Seiyaku Co., Ltd.), TecPolymer MB (manufactured by Sekisui Plastics Co., Ltd.), Fine Powder MP (manufactured by Soken Chemical & Engineering Co., Ltd), and the like), divinylbenzene-based resins, synthetic silica beads, polyurethane-based resins, benzoquanamine resins, melamine resins, phenol-based resins, fluorine-based resins and the like; and inorganic powders such as talc, sericite, mica, kaolin, iron oxide red, clay, bentonite, anhydrous silic acid, mica and the like.

The powder form may be any of sphere, pillar, plate, needle and the like, and a spherical form is preferable from the standpoint of easy slipperiness. The sphericity of a powder is not particularly restricted, and it is preferable to use a power having a form as close to real sphere as possible since if the sphericity increases, the dynamic friction coefficient decreases and sliding feeling of skin increases.

It is preferable that the powder has an average particle size (laser diffraction/scattering method) of 0.05 to 50 $\mu$m, particularly of 0.5 to 50 $\mu$m.

These powders may also be those obtained by a hydrophobicization treatment such as a silicone treatment, fluorine treatment, metal soap treatment, fatty acid treatment and the like.

The powder may be used in combination of two or more, and it is preferable that powders are contained in an amount of 0.1 to 40%, particularly of 1 to 20%, further of 2 to 8% based on the whole composition since then a sufficient effect is obtained and a whitening tendency does not occur after application.

As the oily component, there are listed silicone oils such as dimethylpolysiloxane, methylpolysiloxane, dimethylcyclopolysiloxane, methylhydrogenpolysiloxane and the like; hydrocarbons such as solid or liquid paraffin, crystal oil, ceresin, ozokerite, montan wax and the like; vegetable or animal fats and oils and waxes such as olive, mineral wax, carnauba wax, lanolin, whale wax and the like; further, fatty acids and esters thereof such as stearic acid, palmitic acid, oleic acid, glycerin monostearic acid, glycerin distearic acid, glycerin monooleic acid, isopropyl myristic acid, isopropyl stearic acid, butyl stearic acid, dicapric acid neopentyl glycol and the like; higher alcohols such as cetyl alcohol, stearyl alcohol, palmityl alcohol, hexyldodecyl alcohol and the like. Preferably, isopropyl myristic acid is exemplified.

When an oily component is used, it is preferable that the oily component is contained in a body deodorant composition in an amount of 0.05 to 10%, preferably of 0.1 to 5%.

When the body deodorant composition of the present invention is odorized, odorization is preferably effected with a mixed perfume containing the following perfume substances since an effect of deodorizing a discomfort odor is reinforced. These perfume substances are the same as for the above-mentioned hair cosmetic, and preferably compounded in the same amount.

Particularly, of these perfume substances, $\alpha$-pinene, $\beta$-pinene, methylanthranylate, isobutylquinoline, eugenol, aldehyde C-10, coumarin, vanillin, trypral, cis-3-hexenol, $\alpha$-ionone, $\beta$-ionone, $\gamma$-ionone, $\alpha$-isomethylionone, allylionone, $\alpha$-methylionone, $\beta$-methylionone, $\gamma$-methylionone, $\alpha$-irone, $\beta$-irone, $\gamma$-irone, methylionone-G, Sandalmysolecore, aldehyde C-14 beach, $\alpha$-Damaskon, $\beta$-Damaskon, $\gamma$-Damaskon, $\alpha$-Dynaskon, $\beta$-Dynaskon, Lilial, Chuberose, Caranal, Anbroxane, p-cresol, Malakja, Mosscins, Olivanamresinoid, geranylnitrile, phenoxyethyl alcohol, Florosa, heliotropin, anysil acetate, anysilacetone, acetyl eugenol, acetyl isoeugenol, pentalide, and cyclohexyl salicylate have an excellent effect in masking of a body odor.

Of these perfume substances, 1-carbon, geraniol, citral, thimol, 1,8-cineole, peppermint oil, spearmint oil, lemon grass oil and hiba oil have an antimicrobial activity, therefore, they are particularly preferable perfumes since these perfumes suppress generation of a discomfort order due to proliferation of microorganisms and the like from sebum and sweat components.

The body deodorant composition of the present invention is used in the form of aerosol, pump spray, stick, rollon and the like in addition to liquid forms such as lotion, gel and the like, and impregnated sheets obtained by impregnating a body deodorant composition into a substrate such as non-woven fabric and the like are also preferable.

When the body deodorant composition of the present invention is used in the form of an impregnated sheet, the material of the sheet is non-woven fabric, cloth or vegetable fiber, and materials obtained by complexing them may also be permissible. The impregnated sheet is used in wet condition as a body wiping sheet and in dry condition as a shoe sole, and further, an adhesive layer is provided on one surface of the sheet and the sheet is pasted directly on the skin or pasted to clothes.

EXAMPLES

Reference Example 1

To 20 g (0.116 mol) of commercially available cis-cyclohexane-1,2-dicarboxylic acid (manufactured by Wako Pure Chemical Industries Ltd., hexahydrophthalic acid) was added 123 g of a 5.3 wt % aqueous solution of potassium hydroxide to control the pH value to 7.2, giving a deodorant base agent 1 which was evaluated (first acid dissociation index 4.25, second acid dissociation index 6.74).

Reference Example 2

12.5 g of maleic anhydride and 8 g of cyclopentadiene were dissolved in 100 ml of toluene, and the mixture was heated while stirring at 120° C. for 2 hours in an autoclave. Toluene was distilled off to obtain 18 g (0.116 mol) of a 5-norbornene-2,3-dicarboxylic acid anhydride. To this was added 125 g of a 3.7 wt % sodium hydroxide aqueous solution to control the pH value to 7.1, giving a deodorant base agent 2 which was evaluated (first acid dissociation index 4.16, second acid dissociation index 6.23).

Example 1

Deodorization Effect on Ammonia Odor

Into a schale having a diameter of 4 cm was added 250 mg of the deodorant base agents obtained in Reference Examples 1 and 2, and 50 mg of a 1% ammonia aqueous solution was dropped thereon. The above-mentioned schale was allowed to stand still in a 2.5 liter dessicator for 20 minutes, then, the ammonia concentration (S) was measured by a Kitagawa type gas detector. Further, a schale containing no deodorant base agent was used as a blank 1 and a schale containing 250 mg of water added instead of a deodorant base agent was used as a blank 2, and the ammonia concentration was measured likewise. The ammonia concentration of the blank 1 was represented by C, and the deodorization rate was calculated according to the following formula. As Comparative Example 1, the deodorization effect on an ammonia odor was measured likewise in Example 1 using 250 mg of a solution obtained by dissolving 28 g (0.116 mol) of lauryl methacrylate which is a known deodorant base agent in 115 g of diethylene glycol monoethyl ether. As Comparative Example 2, to 13.7 g (0.116 mol) of succinic acid having a difference of acid dissociation index of less than 1.7 (first acid dissociation index 4.00, second acid dissociation index 5.25) was added 127 g of a 5.3 wt % sodium hydroxide aqueous solution to control the pH value to 7.0, and deodorization effect on an ammonia odor was measured likewise in Example 1 using 250 mg of the resulted solution. The results are shown in Table 3.

(Measurement Method of Deodorization Ratio)

Deodorization rate $(\%) = [(C-S)/C] \times 100$

S: ammonia gas concentration after 20 minutes (ppm)
C: ammonia gas concentration of blank 1 (ppm)

TABLE 3

| Deodorant base agent | Deodorization rate |
|---|---|
| Deodorant base agent 1 | 79% |
| Deodorant base agent 2 | 88% |
| Blank 1 | 0% |
| Blank 2 | 9% |
| Comparative Example 1 | 10% |
| Comparative Example 2 | 33% |

Example 2

Deodorization Effect on Mercaptan

Filter paper having a length of 7 cm and a width of 0.5 cm was impregnated with 150 mg of a deodorant base agent, subsequently, the same filter paper was impregnated with 50 mg of a 0.0002% solution of methylmercaptan in propylene glycol. The filter paper was placed in erected condition in a 3 liter beaker and wrapping film was covered on it and left for 20 minutes, then, a odor filling the beaker was subjected to sensory evaluation. The strength of the odor of methylmercaptan at the initial was defined as 3, and odors after 20 minutes were evaluated by three examiners based on four grades from 0 to 3, and the average value thereof was calculated and the first decimal was rounded off to give a deodorization effect. The deodorant base agent used is the same as in Example 1. The results are shown in Table 4.

TABLE 4

| Deodorant base agent | Evaluation of odor |
|---|---|
| Deodorant base agent 1 | 2 |
| Deodorant base agent 2 | 1 |
| Blank 1 | 3 |
| Blank 2 | 3 |
| Comparative Example 1 | 3 |
| Comparative Example 2 | 3 |

Example 3

Deodorization Effect on Lower Fatty Acid

A odor was evaluated in the same manner as in Example 2 excepting use of 150 mg of a 1% aqueous solution of a lower fatty acid mixture prepared by mixing isovaleric acid, acetic acid and 3-methyl-2-hexenic acid at a ratio of 20/60/20. The results are shown in Table 5

TABLE 5

| Deodorant base agent | Evaluation of odor |
|---|---|
| Deodorant base agent 1 | 1 |
| Deodorant base agent 2 | 1 |

TABLE 5-continued

| Deodorant base agent | Evaluation of odor |
|---|---|
| Blank 1 | 3 |
| Blank 2 | 3 |
| Comparative Example 1 | 2 |
| Comparative Example 2 | 2 |

Example 4

Preparation and Deodorization Effect of Deodorant for Fiber Product

Liquid deodorants 1 to 7 shown in Table 6 were prepared. The liquid deodorant was controlled to pH 7 with N/10 NaOH. The deodorization ability of these liquid deodorants was checked by the following method. The results are shown in Table 6.

<Details of Components Used in Deodorant>
a-1: cis-cyclohexane-1,2-dicarboxylic acid (manufactured by Wako Pure Chemical Industries Ltd., hexahydrophthalic acid)
a-2: deodorant base agent 2 in Reference Example 2
a-3: alkenylsuccinic acid carrying an alkenyl group having 12 carbon atoms (first acid dissociation index 4.06, second acid dissociation index 6.01)
antiseptic and antifungal agent 1: Proxel BDN (trade name, manufactured by Zeneka)
ethanol: 8-acetylated saccharose-denatured ethanol
perfume A: mixture of 40 parts by weight of peppermint oil [Pepper Madras RECT (manufactured by I.P.CALLISON & SONS INC.)], 20 parts by weight of limonene and 40 parts by weight of 2-methyl-2,4-dihydroxybutane <Preparation of Deodorization Object>

Preparation of Tobacco Odor Fiber Product

On one wall of a sealed smoking room of 5 m×5 m×5 m, 2003# cotton cloth of 1 m×1 m was suspended vertically to the floor so that the height from the floor to the top edge of the cloth was 3 m. In this smoking room, 10 males smoked each three cigarettes during 2 hours. Then, the above-mentioned cloth was used in the form of a test sample of 20 cm×20 cm for experiments.

Preparation of Sweat Odor Fiber Product

Underwears worn by 10 males for 24 hours (half sleeve under shirt manufactured by Gunze Ltd., Gunze YG) were put into a vinyl bag which was then sealed, and allowed to stand for 3 days in a room. Then, the underwears were cut into 20 cm×20 cm to give test samples used in experiments.

<Deodorization Method>

A manual spray vessel from which the content, 400 ml of a smoother for iron manufactured by Kao Corp. had been removed was washed until no odor, and dried under an ordinary atmosphere (per one stroke, 0.3 g spray, and adhered area 420 $cm^2$, when sprayed along horizontal direction from 15 cm distant place) into which was then charged 400 ml of the liquid deodorant shown in Table 6. The deodorant was sprayed twice to the above-mentioned deodorization object so that the liquid was spread to the whole surface, and dried under an ordinary atmosphere.

(Evaluation of Deodorization Ability)

10 males and females (each 5) of thirties were allowed to smell odors of deodorization objects, and evaluation was conducted according to the following six-stage odor strength indication method, and the average point was calculated. An average point of 0 or more and less than 1 was represented by ⊚, 1 or more and less than 2 was represented by ○, 2 or more and less than 3 was represented by Δ, and 3 or more and 5 or less was represented by X. ⊚ or ○ is preferable.

0: no odor
1: slight odor is smelt, though the smell source is unknown
2: smell source is known, weak odor which is easily recognized (recognition threshold level)
3: odor which is clearly recognized
4: strong odor
5: unbearably strong odor

TABLE 6

| | | Liquid deodorant | | | | | | |
|---|---|---|---|---|---|---|---|---|
| | | 1 | 2 | 3 | 4 | 5 | 6 | 7 |
| Components compounded (wt %) | | | | | | | | |
| a-1 | | 1 | | | 0.5 | | | |
| a-2 | | | 1 | | | | | |
| a-3 | | | | 1 | 1 | | | |
| Lauryl methacrylate | | | | | | 1 | | |
| Lauryldimethylaminde oxide | | | | | 0.5 | | | |
| Antiseptic/antifungal agent 1 | | 0.05 | 0.05 | 0.05 | 0.05 | 0.05 | 0.05 | 0.05 |
| Ethanol | | 5 | 5 | 5 | 5 | 5 | 5 | 5 |
| Perfume A | | 0.02 | 0.02 | 0.02 | 0.1 | 0.02 | 0.02 | |
| Ion exchanged water | | balance | balance | balance | balance | balance | balance | balance |
| Total | | 100 | 100 | 100 | 100 | 100 | 100 | 100 |
| pH | | 7 | 7 | 7 | 7 | 7 | 7 | 7 |
| Deodorization ability | | | | | | | | |
| tobacco odor | Directly after treatment | ⊚ | ⊚ | ○ | ⊚ | Δ | Δ | Δ |
| | 24 hours after | ○ | ○ | ○ | ○ | Δ | Δ | x |
| Sweat odor | Directly after treatment | ○ | ⊚ | ○ | ⊚ | ○ | Δ | Δ |
| | 24 hours after | ○ | ○ | ○ | ⊚ | Δ | Δ | x |

<Results>

The liquid deodorants 1 to 4, products of the present invention showed excellent deodorization effects, and showed a tendency of small change of odor by leaving after treatment.

Example 5

Preparation and Deodorization Effect of Deodorant for Space

Liquid deodorants 8 to 14 shown in Table 7 were prepared. The liquid deodorant was controlled to pH 7 with N/10 NaOH. A mist type spray vessel having a spray ability of 0.2 ml/stroke was filled with 20 ml of the resulted liquid deodorant, and the deodorant was sprayed into a deodorization space according to the following deodorization experiment method, then, the deodorization ability was checked. The results are shown in Table 7.

<Details of Components Used in Deodorant>
a-1: the same as in Example 4
a-3: the same as in Example 4
a-4: alkenylsuccinic acid carrying an alkenyl group having 14 carbon atoms (first acid dissociation index 4.01, second acid dissociation index 6.12)
AG1: alkylglucoside having a degree of polymerization of 1.5 obtained by adding an alkyl group having a carbon number derived from palm oil to a site of 1-position of a sugar
AG2: alkylglucoside having a degree of polymerization of 1.3 obtained by adding a brached alkyl group having 9 carbon atoms to a site of 1-position of a sugar
AES: polyoxyethylene alkyl ether sulfate eater sodium salt (alkyl group is linear and has 12 carbon atoms, EOp is 2.5)
antiseptic and antifungal agent 1: the same as in Example 4
antiseptic and antifungal agent 2: metylparavene
ethanol: the same as in Example 4
perfume B: mixture of 80 parts by weight of a mixture of peppermint oil [Pepper Madras RECT (manufactured by I.P.CALLISON & SONS INC.)]/1-menthone/eucalyputus oil [Eucalyputus Oil Citriodora (manufactured by CHARABOT & DARGEVILLE)]/cis-3-hexenol=60/30/8/2 (by weight), and 20 parts of dipropylene glycol
perfume C: mixture of 80 parts by weight of a mixture of cis-3-hexenol/orange oil/lemon oil/geranium oil=2/60/30/8 (by weight), and 20 parts of dipropylene glycol <Deodorization Experiment Method>

In a space of a lateral length of 3.5 m, a longitudinal length of 4.5 m and a height of 2.5 m being able to effect exhaust and having a sufficient air conditioning apparatus, tobacco odor was evaluated in the space directly after smoking of 5 cigarettes, and cooking odor was evaluated in the space directly after meat panfry. The temperature was set at 25° C. An examiner stood in the center of the room containing a tobacco odor or cooking odor, and held the spray at the height of eyes and sprayed the deodorant toward four corners of the room each twice and eight times in total, and the odor directly after spray was evaluated according to the following deodorization ability evaluation method.

<Evaluation of Deodorization Ability>

The deodorization ability on an order was evaluated by one sensitive female on thirties according to the six-stage odor strength indication method in Example 4.

TABLE 7

| | | Liquid deodorant | | | | | | |
|---|---|---|---|---|---|---|---|---|
| | | 8 | 9 | 10 | 11 | 12 | 13 | 14 |
| Components compounded (wt %) | | | | | | | | |
| a-1 | | 0.2 | | | | | | |
| a-3 | | | 0.25 | 0.06 | | 0.03 | | |
| a-4 | | | | | 0.4 | | | |
| AG1 | | 0.5 | 1 | 0.5 | | 0.3 | 0.5 | 0.3 |
| AG2 | | | 0.5 | | 1 | | | |
| AES | | | 0.3 | | | 0.03 | | |
| Antiseptic/antifungal agent 1 | | | 0.1 | | | | | |
| Antiseptic/antifungal agent 2 | | | | 0.1 | | | 0.1 | |
| Citric acid | | | | 0.1 | | | 0.1 | |
| Benzoic acid | | 0.1 | | | 0.1 | | | |
| Ethanol | | 7 | 7 | 5.5 | 5.5 | 10 | 5.5 | 7 |
| Perfume B | | 0.5 | 1 | 0.3 | 0.05 | | 0.3 | |
| Perfume C | | | | | | 0.1 | | 0.1 |
| Ion exchanged water | | balance | balance | balance | balance | balance | balance | balance |
| Total | | 100 | 100 | 100 | 100 | 100 | 100 | 100 |
| pH | | 7 | 7 | 7 | 7 | 7 | 7 | 7 |
| Deodorization ability | | | | | | | | |
| Tobacco odor | Directly after treatment | 0 | 0 | 0 | 1 | 0 | 1 | 1 |
| | 24 hours after | 1 | 1 | 1 | 1 | 1 | 3 | 3 |
| Cooking odor | Directly after treatment | 0 | 0 | 0 | 0 | 0 | 2 | 2 |
| | 24 hours after | 1 | 1 | 1 | 1 | 1 | 3 | 3 |

<Results>

The liquid deodorants 8 to 12, products of the present invention shows excellent deodorization effects.

Example 6

The hair cosmetics 1 to 6 shown in Table 8, namely the products 1 to 4 of the present invention and comparative products 1 to 3 shown in Table 6 were prepared, and the deodorization effects of the present invention were evaluated according to the following methods.

Hair-adhered Odors (Tobacco Odor, Cooking Odor, Sweat Odor)

Preparation of Tobacco Odor Hair-adhered Sample

On one wall of a sealed smoking room of 5 m×5 m×5 m kept under a temperature of 25° C. and a humidity of 65 HR, 20 g of a staple (15 cm) made from human hairs was suspended vertically to the floor so that the height from the floor to the top of the staple was 3 m. In this smoking room, 10 males smoked each three cigarettes during 2 hours. The odor-adhered staple was used as a test sample.

Preparation of Cooking Odor Hair-adhered Sample

On one wall of a sealed smoking room of 5 m×5 m×5 m kept under a temperature of 25° C. and a humidity of 65 HR, 20 g of a staple (15 cm) made from human hairs was suspended vertically to the floor so that the height from the floor to the top of the staple was 3 m. In this smoking room, each three kinds of fishes and meats were cooked for 30 minutes. The cooking odor generated in this cooking was adhered to hairs to be used as a test sample.

Preparation of Sweat Odor Hair-adhered Sample

In a sealed training room of 10 m×10 m×10 m kept under a temperature of 25° C. and a humidity of 65 HR, about 7 g (15 cm) of a staple was bonded in three units to head parts of five males and five females, they were allowed to effect running training for about 1 hour, and after sweating, three staples collected from a head part were gathered to give one staple and ten of the latter staples were prepared to be as the test sample.

Deodorization Test (1) Deodorization Method and Evaluation

The hair cosmetic of the present invention prepared by an ordinary method was applied in an amount of 1 g on a deodorization object sample, and spread on the whole surface by a brush, then, deodorization and masking effects were evaluated directly after the treatment and next day (24 hours after). 10 examiners, 5 being male and 5 being female, of twenties to forties were allowed to smell odors of the deodorization/masking object, and evaluations were conducted according to the following six grade criteria, and the average point was calculated. An average point of 0 or more and less than 1 was represented by ◎, 1 or more and less than 2 was represented by ○, 2 or more and less than 3 was represented by Δ, and 3 or more was represented by X.

(2) Evaluation criteria

0: no odor
1: complete deodorization or masking
2: almost complete deodorization or masking, or masking odor
3: slight discomfort odor
4: discomfort odor (slight deodorization or insufficient masking)
5: clear discomfort odor (deodorization or insufficient masking)

TABLE 8

Hair cosmetic

| | Product of the invention 1 Hair cosmetic 1 | Comparative product 1 Hair cosmetic 5 | Product of the invention 2 Hair cosmetic 2 | Comparative product 2 Hair cosmetic 6 | Product of the invention 3 Hair cosmetic 3 | Product of the invention 4 Hair cosmetic 4 | Comparative product 4 Hair cosmetic 7 |
|---|---|---|---|---|---|---|---|
| Components compounded (wt %) | | | | | | | |
| cis-1,2-cyclohexanedicarboxylic acid | 1.0 | — | 1.0 | — | — | — | — |
| Trans-1,2-cyclooctanedicarboxylic acid | — | — | — | — | 1.0 | 1.0 | — |
| Tartaric acid | | | | | | | 1.0 |
| Nylon powder | 3.0 | 3.0 | 3.0 | 3.0 | 3.0 | 3.0 | 3.0 |
| Styrene/stearyl methacrylate/divinylbenzene copolymer | 0.1 | 0.1 | 0.1 | 0.1 | 0.1 | 0.1 | 0.1 |
| Methylpolysiloxane (Silicone KT-5, manufactured by GE Toshiba Silicones) | 1.5 | 1.5 | 1.5 | 1.5 | 1.5 | 1.5 | 1.5 |
| Carobxyvinyl polymer (Carbopol 981, manufactured by B. F. Goodrich | 0.2 | 0.2 | 0.2 | 0.2 | 0.2 | 0.2 | 0.2 |
| Potassium hydroxide | 0.07 | 0.07 | 0.07 | 0.07 | 0.07 | 0.07 | 0.07 |
| Dipotassium glycyrrhizinate | 0.1 | 0.1 | 0.1 | 0.1 | 0.1 | 0.1 | 0.1 |
| 1,3-butylene glycol | 1.0 | 1.0 | 1.0 | 1.0 | 1.0 | 1.0 | 1.0 |
| Ethanol | 50.0 | 50.0 | 50.0 | 50.0 | 50.0 | 50.0 | 50.0 |
| Propyl p-oxybenzonate | 0.1 | 0.1 | 0.1 | 0.1 | 0.1 | 0.1 | 0.1 |
| Purified water | balance | balance | balance | balance | balance | balance | balance |
| Perfume composition D | 1.0 | 1.0 | — | — | 1.0 | — | 1.0 |
| pH | 5.8 | 5.8 | 5.8 | 5.8 | 5.8 | 5.8 | 5.8 |
| Deodorization ability | | | | | | | |

TABLE 8-continued

Hair cosmetic

|  |  | Product of the invention 1 Hair cosmetic 1 | Comparative product 1 Hair cosmetic 5 | Product of the invention 2 Hair cosmetic 2 | Comparative product 2 Hair cosmetic 6 | Product of the invention 3 Hair cosmetic 3 | Product of the invention 4 Hair cosmetic 4 | Comparative product 4 Hair cosmetic 7 |
|---|---|---|---|---|---|---|---|---|
| Tobacco odor | Directly after treatment | ⊙ | ○ | ○ | Δ | ⊙ | ○ | ○ |
|  | 24 hours after | ○ | Δ | ○ | x | ○ | ○ | Δ |
| Cooking odor | Directly after treatment | ⊙ | ○ | ○ | Δ | ⊙ | ○ | ○ |
|  | 24 hours after | ○ | Δ | ○ | x | ○ | ○ | Δ |
| Sweat odor | Directly after treatment | ⊙ | ○ | ○ | Δ | ⊙ | ○ | ○ |
|  | 24 hours after | ○ | Δ | ○ | x | ○ | ○ | Δ |

Any of the products 1 to 4 of the present invention, namely, the hair cosmetics 1 to 4 manifested an excellent deodorization effect on tobacco odors, cooking odors and sweat odors adhered to hairs.

A perfume composition D having the following formulation (Table 9) was prepared, and hair cosmetics of Examples 7 to 17 were produced.

TABLE 9

| Perfume composition D | (Parts by weight) |
|---|---|
| Lemon oil | 10 |
| Bergamot oil | 100 |
| Dihydromicenol | 155 |
| cis-3-hexenol | 15 |
| Tripranol | 4 |
| Allylamylglycolate | 15 |
| Lavender oil | 40 |
| Lynalyl acetate | 75 |
| Eugenol | 10 |
| α-Damaskon (50% dipropylene glycol solution) | 4 |
| Geraniol | 20 |
| Phenoxyethyl alcohol | 20 |
| Edion | 100 |
| Methylanthanilate (10% dipropylene glycol solution) | 5 |
| Lilial | 70 |
| Linalool | 200 |
| β-ionone | 50 |
| Caranal (10% dipropylene glycol solution) | 5 |
| Vanillin (10% dipropylene glycol solution) | 3 |
| Coumarin | 7 |
| Dipropylene glycol | 107 |
| Total | 1000 |

Example 7 (Lotion)

| | |
|---|---|
| Cis-1,2-cyclohexanedicarboxylic acid | 1.0 |
| Styrene/methyl methacrylate/diemthylpolysiloxane graft copolymer | 3.5 |
| Methylpolysiloxane (Silicone KF-96A, manufactured by Shin-Etsu Silicone K.K.) | 1.0 |
| Acrylic acid/alkyl methacrylate copolymer (PEMULEN TR-1, manufactured by B. F. Goodrich) | 0.2 |
| L-arginine | 0.2 |
| di-α-tocopherol acetate | 0.1 |
| PEG600 | 1.0 |
| 1-menthole | 0.3 |
| Ethanol | 30.0 |
| Ethyl p-oxybenzoate | 0.2 |
| Perfume composition D | 0.1 |
| Purified water | Total 100.0 |

Example 8 (Hair Nourishing Agent)

| | |
|---|---|
| Cis-1,2-cyclohexanedicarboxylic acid | 1.0 |
| Nicotinic amide | 0.1 |
| di-α-tocopherol acetate | 0.05 |
| β-glycyrrhetic acid | 0.1 |
| Swertia herb extract | 1.2 |
| Carrot extract | 0.3 |
| Hyperricum erectum extract | 0.5 |
| 1-menthole | 0.2 |
| Ouki extract | 0.3 |
| Polyoxyethylene (25EO) hardened castor oil | 0.2 |
| Stearyltrimethylammonium chloride (Coatamine 86W, manufactured by Kao Corp.) | 0.5 |
| Ethanol | 50.0 |
| Perfume composition D | 0.1 |
| Purified water | Total 100.0 |
| Carbonate gas: spray agent (raw liquid/spray agent) | 98/2 |

Example 9 (Tonic)

| | |
|---|---|
| Cis-1,2-cyclohexanedicarboxylic acid | 1.0 |
| Stearyltrimethylammonium chloride (Coatamine 66W, manufactured by Kao Corp.) | 0.2 |
| Polyoxyethylene (25EO) hardened castor oil | 0.1 |
| Polyoxyethylene/polyoxypropylene stearyl ether | 0.7 |
| di-α-tocopherol acetate | 0.05 |
| Dipotasium glycyrrhizinate | 0.1 |
| Triclosane | 0.1 |
| Ethanol | 60.0 |
| Perfume composition D | 0.1 |
| Purified water | Total 100.0 |

Example 10 (shampoo)

| | |
|---|---|
| Cis-1,2-cyclohexanedicarboxylic acid | 1.0 |
| Sodium polyoxyethylene (3) lauryl ether sulfate | 10.0 |
| Sodium lauryl sulfate | 5.0 |
| Polyoxyethylene (15) lauryl ether | 1.0 |
| Lauric acid diethanol amide | 1.0 |
| Lauric acid amide propyl betaine | 1.0 |
| Stearylmethylammonium chloride | 0.1 |
| Perfume composition D | 0.4 |
| Purified water | Total 100.0 |

Example 11 (Rinse)

| | |
|---|---|
| Cis-1,2-cyclohexanedicarboxylic acid | 1.0 |
| Stearyltrimethylammonium chloride | 1.1 |
| Cetanol | 3.0 |
| Isopropyl palmitate | 0.5 |
| Dimethylpolysiloxane emulsion | 4.0 |
| Hydroxyethyl cellulose | 0.1 |
| Perfume composition D | 0.3 |
| Purified water | Total 100.0 |

Example 12 (Spray)

| | |
|---|---|
| Cis-1,2-cyclohexanedicarboxylic acid | 1.0 |
| Glycerine | 2.0 |
| Cetanol | 4.0 |
| Light liquid isoparaffin (Isosol 400 manufactured by Nisseki Mitsubishi K.K.) | 4.0 |
| Polyoxyethylene (20EO) isocetyl ether | 0.5 |
| Isostearyl glyceryl ether | 2.0 |
| Dimethylpolysiloxane | 1.0 |
| 95% ethanol | 85.4 |
| Perfume composition D | 0.1 |
| Purified water | Total 100.0 |

Example 13 (Hair Mist)

| | |
|---|---|
| Cis-1,2-cyclohexanedicarboxylic acid | 1.0 |
| Polyoxyethylene hardened castor oil | 0.2 |
| Stearyltrimethylammonium chloride (28%) | 0.5 |
| Softanol | 0.1 |
| Glycerine | 3.0 |
| 95% ethanol | 10.0 |
| Perfume composition D | 0.05 |
| Purified water | Total 100.0 |

Example 14 (Hair Cream)

| | |
|---|---|
| Cis-1,2-cyclohexanedicarboxylic acid | 1.0 |
| Dimethylpolysiloxane | 5.0 |
| Sorbitol | 10.0 |
| α-monoisostearyl glyceryl ether | 1.0 |
| Higher alcohol (allyl alcohol) | 7.0 |
| Propylene glycol | 2.0 |
| 95% ethanol | 2.0 |
| Polyoxyethylenesorbitane monooleate | 4.0 |
| Glycerol monostearate | 2.0 |
| Perfume composition D | 0.1 |
| Purified water | Total 100.0 |

Example 15 (Hair Nourishing Agent)

| | |
|---|---|
| Cis-1,2-cyclohexanedicarboxylic acid | 1.0 |
| 95% ethanol | 60.0 |
| 1-menthol | 0.15 |
| Nicotinic amide | 0.15 |
| β-glycyrrhetic acid | 0.12 |
| Stearylamine | 1.5 |
| Ouki extract | 0.95 |
| Hypericum erectum extract | 0.09 |
| Feeling improving agent | 0.2 |
| pH controlling agent | 0.2 |
| Perfume composition D | 0.1 |
| Purified water | Total 100.0 |

Example 16 (Hair Nourishing Agent)

| | |
|---|---|
| Cis-1,2-cyclohexanedicarboxylic acid | 1.0 |
| 95% ethanol | 74.0 |
| 1-menthol | 0.7 |
| Decyltetradecyldimethylamine oxide | 0.15 |
| 1,3-butanediol | 0.12 |
| Pantotenyl ethyl ether | 0.4 |
| Nicotinic amide | 0.1 |
| Benzyl nicotinate | 0.01 |
| β-glycyrrhetic acid | 0.2 |
| 1-dodecene | 0.01 |
| Titaniun oxide | 0.5 |
| pH controlling agent | 4.5 |
| Perfume composition D | 0.1 |
| Purified water | Total 100.0 |

Example 17 (Hair Liquid)

| | |
|---|---|
| Cis-1,2-cyclohexanedicarboxylic acid | 1.0 |
| Acrylic amide/acrylic acid/methoxy methacrylate polyethylene glycol copolymer | 2.0 |
| Polyoxypropylene butyl ether phosphoric acid (21 P.O.) | 7.0 |
| Polyoxyethylene hardened castor oil | 5.0 |
| Dipropylene glycol | 3.0 |
| Polyoxyethylene isocetyl ether (20 EO) | 0.4 |
| Diethylene glycol monoethyl ether | 0.6 |
| 2-hydroxy-4-methoxybenzophenone-5-sulfonic acid | 0.1 |
| Perfume composition D | 0.3 |
| Sodium hydroxide | 3.0 |
| 95% ethanol | 60.0 |
| Buffering agent | 0.4 |
| Hair permeating agent | 0.2 |
| Purified water | Total 100.0 |

Any of the hair cosmetics of Examples 7 to 17 manifested an excellent deodorization effect on tobacco odors adhered to hairs, cooking instruments for grilling and the like, and a sweat odor.

Example 18

A body deodorant composition shown in Table 10 was prepared, and subjected to sensory evaluation by 10 examiners afraid of foot order and the results are shown below.

The odor of toe was smelt directly after removal of socks worn for 8 hours, and this level was used as control. Then, without an interval, 1 g of the body deodorant composition was sprayed uniformly on toe parts using a pump spray, and the deodorization effect obtained 10 minutes after the application as compared with the control was evaluated according to the following criteria.

| Evaluation criteria | Evaluation point |
|---|---|
| Deodorized | 4 |
| Slightly deodorized | 3 |

-continued

| Evaluation criteria | Evaluation point |
|---|---|
| Not so deodorized | 2 |
| Not deodorized | 1 |

The average evaluation points by 10 examiners were classified into the following ranks.

| Average evaluation points | Rank |
|---|---|
| 3.5 to 4.5 | ⊚ |
| 2.5 to 3.4 | ○ |
| 1.5 to 2.4 | Δ |
| 1.0 to 1.4 | x |

TABLE 10

|  | Product of the invention Example 18 | Comparative Example 3 |
|---|---|---|
| Cis-cyclohexane-1,2-dicarboxylic acid | 5.0(0.029 mole)% | — |
| Succinic acid | — | 3.4(0.029 mole) |
| Potassium hydroxide (pH controlling agent) | Suitable amount | Suitable amount |
| Purified water | balance | balance |
| pH | 7.0 | 7.0 |
| Deodorization effect rank | ⊚ | Δ |

The product of the present invention, namely, the product in Example 18 manifested an extremely excellent deodorization effect on a foot odor.

Example 19

Body Lotion

| Cis-cyclohexane-1,2-dicarboxylic acid | 3.0% |
|---|---|
| Talc | 3.0 |
| Triethanolamine | suitable amount |
| Propylene glycol | 1.0 |
| Perfume | 0.1 |
| Ethanol | 10 |
| Purified water | balance |
| pH 6.0 | |

Example 20

Rollon Body Deodorant Composition

The following components were prepared and charged into a rollon vessel.

| Alkenylsuccinic acid (C12) | 5.0% |
|---|---|
| Isopropylmethylphenol | 0.2 |
| Hydroxypropyl cellulose | 2.0 |
| Triethanolamine | suitable amount |
| Glycerine | 0.5 |
| Perfume | 0.05 |
| Ethanol | 50 |
| Purified water | balance |

Example 21

Deodorant Stick

| Potassium cis-cyclohexane-1,2-dicarboxylate[1] | 3.0% |
|---|---|
| Aluminumhydroxy chloride | 15.0 |
| Talc | 10.0 |
| Isopropyl myristate | 20.0 |
| Stearyl alcohol | 12.0 |
| Hardened oil | 4.0 |
| Polyoxyethylene hardened castor oil | 2.0 |
| Sesquistearic acid polyoxyethylene methylglucoside | 1.0 |
| Perfume | 0.1 |

[1]Cis-cyclohexane-1,2-dicarboyxlic acid was neutralized with potassium hydroxide of 1.7-fold equivalent and dried.

Example 22

Deodorant Spray

An aerosol containing raw liquid/spray agent (dimethyl ether)—50/50 by weight was produced using the following components as raw materials.

| Potassium cis-cyclohexane-1,2-dicarboxylate | 1.0% |
|---|---|
| Triclosane | 0.1 |
| 1-menthol | 0.5 |
| Methylparavene | 0.2 |
| Perfume | 0.07 |
| Ethanol | 40.0 |
| Purified water | 58.13 |

Example 23

Deodorization Sheet

The following body deodorant composition was prepared, and 4.5 g of this composition was impregnated into pulp (5×6 cm, two ply, 1.8 g) to produce a deodorant sheet.

| Potassium cis-cyclohexane-1,2-dicarboxylate | 3.0% |
|---|---|
| Triclosane | 0.1 |
| Sodium benzoate | 0.3 |
| Hydroxypropyl cellulose | 0.5 |
| Silicone powder[2] | 5.0 |
| Isopropyl myristate | 2.0 |
| Polyoxyethylene (20) sorbitan monolaurate | 0.5 |
| Perfume | 0.05 |
| Ethanol | 35.0 |
| Purified water | 53.55 |

[2]Silicone KMP590 (manufactured by Shin-Etsu Chemical Co., Ltd.)

Example 24

Deodorant Sheet for Armpit

The following body deodorant composition (2.0 g) was impregnated into non-woven fabric (diameter 70 mm) which was then dried, to produce a deodorant sheet for armpit.

| Potassium cis-cyclohexane-1,2-dicarboxylate[1] | 3.0% |
|---|---|
| Triclosane | 0.1 |

-continued

| | |
|---|---|
| Sodium benzoate | 0.3 |
| Polyether-modified silicone*3) | 0.5 |
| Perfume | 0.05 |
| Ethanol | 35.0 |
| Purified water | 61.05 |

3*)Silicone SH3775C (manufactured by Dow Corning Toray Silicone Co., Ltd.)

Any of the products of the present invention in examples 19 to 24 manifested an excellent deodorization effect.

What is claimed is:

1. A deodorant comprising a deodorant organic dibasic acid, said acid comprising an organic dibasic acid, a salt thereof or combinations thereof,
   wherein said acid has a difference between a first acid dissociation index and a second acid dissociation index of 1.7 or more at 25° C.,
   wherein said second dissociation index is from 6 to 8, and
   wherein said salt is selected from the group consisting of an alkali metal salt, an ammonium salt, a zinc salt, an aluminum salt and mixtures thereof.

2. The deodorant according to claim 1 wherein a water content is from 80 to 99% by weight.

3. A deodorant composition comprising the deodorant according to claim 1 and a surfactant in an amount of 0.01 to 10% by weight.

4. The deodorant composition according to claim 1, further comprising 0.001 to 2.0% by weight of a perfume.

5. A spray mode deodorant article comprising a spray mode vessel filled with the deodorant according to claim 1.

6. A hair cosmetic comprising the deodorant organic dibasic acid according to claim 1.

7. A body cosmetic deodorant comprising the deodorant organic dibasic acid according to claim 1.

8. A skin cosmetic comprising the deodorant organic dibasic acid according to claim 1.

9. A method of deodorizing an object comprising, applying the deodorant organic dibasic acid according to claims 1 to said object.

10. The method according to claim 9 wherein the object is clothes or body.

11. The method according to claim 9 wherein the object is hair or skin.

12. A body deodorant composition comprising the deodorant according to claim 1 and a bactericide or a sweat controlling agent.

13. A sheet comprising the body deodorant according to claim 7.

14. A method of deodorizing a body comprising, pasting the sheet according to claim 13 in a dry or wet condition to said body or wiping said body with the sheet.

15. The deodorant according to claim 1, wherein the organic dibasic acid is cyclohexane-1,2-dicarboxylic acid.

16. The deodorant according to claim 1, wherein the organic dibasic acid is 5-norbornene-2,3-dicarboxylic acid.

17. The deodorant according to claim 1, further comprising an alkyl glycodise having a degree of polymerization of a glycose residue of 1.2 to 1.8 in which one alkyl group or alkenyl group having 8 to 18 carbon atoms is bonded to the 1-position of the glucose.

18. The deodorant according to claim 1, further comprising a monoalkyl dimethylamine oxide comprising bonded units of an alkyl group having 8 to 18 carbon atoms and a fatty amide propyldimethylamine oxide.

* * * * *

UNITED STATES PATENT AND TRADEMARK OFFICE
CERTIFICATE OF CORRECTION

PATENT NO. : 6,780,403 B1  Page 1 of 1
DATED : August 24, 2004
INVENTOR(S) : Yamashita et al.

It is certified that error appears in the above-identified patent and that said Letters Patent is hereby corrected as shown below:

<u>Title page,</u>
Item [87], should read:
-- [87] PCT Pub. No.: WO01/07002
PCT Pub. Date: Feb. 1, 2001 --.

Signed and Sealed this

Twenty-third Day of August, 2005

JON W. DUDAS
*Director of the United States Patent and Trademark Office*